United States Patent [19]
Austin

[11] Patent Number: 4,790,834
[45] Date of Patent: Dec. 13, 1988

[54] EXTERNAL SINGLE-USE CATHETER

[75] Inventor: Gerald W. Austin, Salem, Va.

[73] Assignee: Professional Care Products, Inc., Roanoke, Va.

[21] Appl. No.: 74,051

[22] Filed: Jul. 16, 1987

Related U.S. Application Data

[63] Continuation-in-part of Ser. No. 737,428, May 24, 1985, Pat. No. 4,685,913.

[51] Int. Cl.$^4$ ............................................... A61F 5/44
[52] U.S. Cl. ................................... 604/349; 604/327; 128/767
[58] Field of Search ............... 604/317, 327, 328, 329, 604/332, 333, 335, 346, 347, 348, 349, 350, 351–356; 128/760, 767; 383/5, 38, 93

[56] References Cited

U.S. PATENT DOCUMENTS

| | | | |
|---|---|---|---|
| 2,863,457 | 12/1958 | Barach | 604/350 |
| 2,976,869 | 3/1961 | Silverstone et al. | 604/353 |
| 3,030,958 | 4/1962 | Levin | 604/347 |
| 3,364,932 | 1/1968 | Beach | 604/352 |
| 3,403,682 | 10/1968 | McDonell | 604/352 |
| 3,613,123 | 10/1971 | Langstrom | 604/347 |
| 3,788,324 | 1/1974 | Lim | 604/352 |
| 4,387,726 | 6/1983 | Denard | 604/353 |

FOREIGN PATENT DOCUMENTS

| | | | |
|---|---|---|---|
| 84/02070 | 6/1984 | PCT Int'l Appl. | 604/349 |
| 2016929 | 9/1979 | United Kingdom | 604/353 |
| 2167304 | 5/1986 | United Kingdom | 604/350 |

*Primary Examiner*—Stephen C. Pellegrino
*Assistant Examiner*—Mario Costantino
*Attorney, Agent, or Firm*—Burns, Doane, Swecker & Mathis

[57] ABSTRACT

The present invention provides an external single-use, disposable male catheter, comprising a pliable plastic container having a closed end and an opening so as to receive a fluid, an absorbent, and an interior partition separating the closed end and the opening to retain the absorbent. The partition is water-permeable and is optionally disintegrable when contacted with urine. Additionally, a closure means is provided which includes a layer of foam attached to the plastic at the opening and having a vapor-permeable adhesive on the other side for adhering to itself and skin.

3 Claims, 3 Drawing Sheets

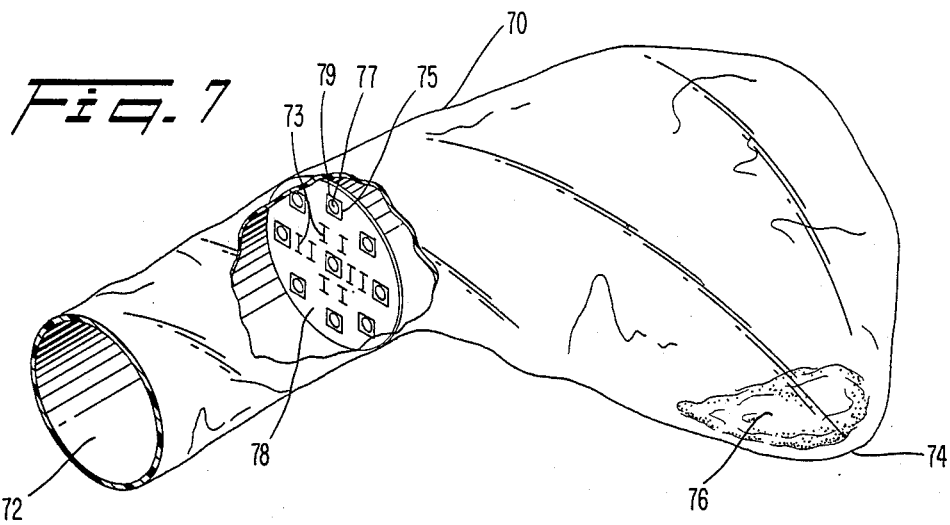
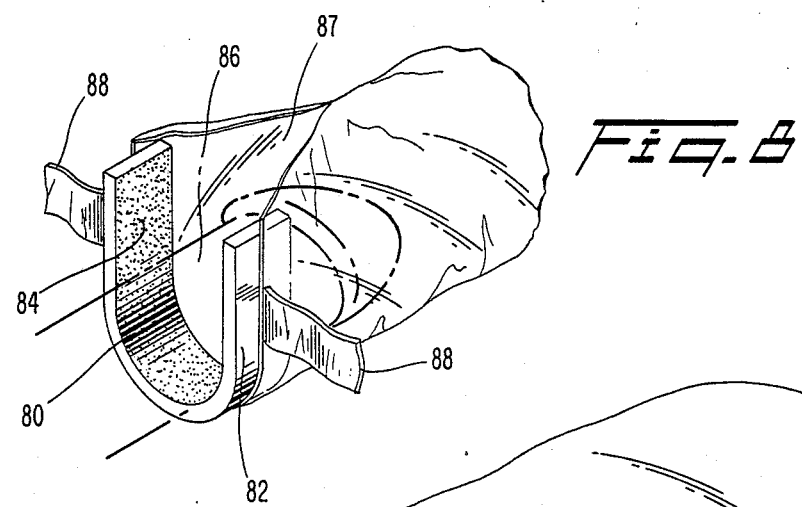
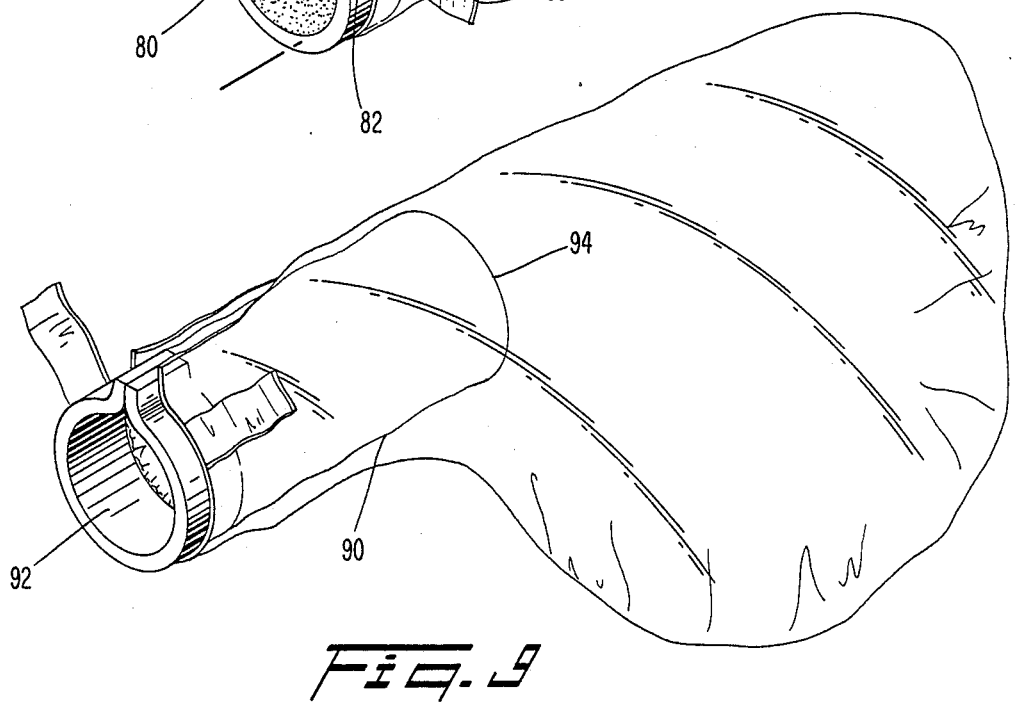

EXTERNAL SINGLE-USE CATHETER

BACKGROUND OF THE INVENTION

This application is a continuation-in-part of application Ser. No. 737,428, filed May 24, 1985 now U.S. Pat. No. 4,685,913.

This invention relates to external catheters for males. In particular, this invention provides a single-use, disposable external catheter for males that provides superior comfort for the user, improved hygienic aspects, and ease of attachment and removal of the device.

A conventional catheter currently in use is the so-called "Texas" male external catheter. This type of external male catheter is a heavy-gauge latex rubber condom with a tube attached to the terminus of the condom. This tube is attached to additional tubing, and, in turn, to a receptacle into which the waste products flow. U.S. Pat. No. 3,364,932 discloses such a condom catheter device.

One problem with this type of catheter is that the catheter remains attached to the patient for extended periods of time. Hence, while the tube and waste receptacle are replaced when necessary, the catheter per se remains in contact with the patient for extended periods of time. This, in turn, leads to hygiene problems due to irritation from perspiration and other bodily secretions which accumulate between the penis and the surrounding condom.

Another problem inherent in such condom catheters is that the patient's movements are restricted due to the tube which carries the urine to the receptacle. In fact, obstruction of the tube, such as by a patient lying on it, will tend to aggravate the hygiene and irritation problems elucidated above.

Still another problem with such condom catheters is that hygiene problems, with respect to both the patient and the nursing staff, are aggravated by the need to remove the tube from the condom catheter when the receptacle is replaced, thereby subjecting the patient and health care staff to exposure to fluids retained in the catheter or the tube or both.

Still another problem with such condom catheter is that the catheter or the closure means, or both, are close-fitting to the penis and not readily flexible. This inflexibility often leads to circulation restriction and general discomfort of the patient upon swelling.

A further problem inherent in such devices is the lack of visual contact with the discharged fluids and with the penis. Instant visual contact to determine if there has been a discharge and if so whether the characteristics of the discharge indicate complications (or lack of complications) is important to the patient's care.

Devices analogous to the catheters noted above are those devices used for incontinent persons. Generally, such devices comprise a bag receptacle of relative toughness, an absorbent, and are attached to the user by means of a strap around the waist. These devices, similarly to the catheters mentioned above, are attached to the user for extended periods of time and therefore lead to hygiene problems. Also, there are exacerbated hygiene problems where the device utilizes a removable absorbent, thereby subjecting the wearer and the remover to contact with the waste products. U.S. Pat. No. 2,864,369 discloses such an incontinence device.

An additional problem is that urine can flow back onto the penis or that an absorbent material soaked with urine can come into contact with the penis. Various devices employ a "flutter valve," which is a liquid-impermeable material forming a narrow slit or hole through which the urine flows out into a collection or absorbtion area. Such devices are disclosed in U.S. Pat. Nos. 1,490,793 and 3,559,651. The devices disclosed therein include a liquid-impermeable material in a shape that telescopes into a flatter valve, thus approximating the close and unhygienic conditions found in the condom catheters. Moreover, the close conditions and liquid-impermeable material can result in the splashing of urine back onto the genitalia.

Yet another problem can occur which has not been addressed fully in the art. With the advent of superabsorbent powders, various commercially available incontinence devices structured as diapers have employed such powders as an absorbent. While no known external catheter has employed such powders, it will be appreciated that during manufacture and shipment, the powder is likely to be well-distributed in the interior of any catheter-type devices or even lost, rather than remaining concentrated in one area. Further, the powder can possibly come into contact with the patient or nursing staff.

Contrary to the devices mentioned above, the device of the present invention provides a single-use, disposable external catheter which is self-contained, thereby eliminating the aforementioned hygiene problems. To avoid such hygiene and irritation problems, the present device comprises a loose-fitting pliable bag such that the only portion in intimate contact with the patient is at the point of closure around the penis. To avoid circulation and swelling problems, the closure is preferably formed of an extensible material which is vapor permeable, thereby avoiding vapor irritation from the waste fluids and allowing vapor exchange between the interior and the exterior of the catheter. For certain applications, however, the closure can be a band of a suitable adhesive on the bag or formed of material that is not permeable to vapor or liquid. The closure means is designed to facilitate selective attachment and removal of the device, as opposed to the belt attachment means of incontinence devices and the attachment means of close-fitting condom catheters. The present device is designed for a single-use and to be disposed of thereafter, thereby alleviating or eliminating intrinsic problems of extended wear catheters and incontinence devices.

With the foregoing in mind, it is an object of this invention to provide a single-use catheter which facilitates professional nursing care of the patient. Further, it is an object of this invention to provide a single-use catheter which is of less expense than alternatives presently in use. Moreover, it is an object of this invention to provide an inexpensive and disposable external catheter for single-use.

It is another object of this invention to provide a single-use male catheter which is self-contained. A further object of this invention is to provide a catheter which alleviates or eliminates hygiene problems, which maintains sanitary conditions with respect to the patient and health care staff and which allows the health care staff to keep the patient's bed and sheets free from odor and staining due to spillage.

A further object of this invention is to provide a single-use male catheter which alleviates or eliminates irritation and urine burn problems inherent in multiple-use catheters.

Still a further object of this invention is to provide a catheter which is easy to selectively attach and remove from the patient and which alleviates or eliminates restriction of the patient's circulation and swelling caused thereby. It is also an object of this invention to provide a catheter which eliminates patient discomfort and which does not restrict the patient's movements when used.

It is yet another object of this invention to provide a catheter which allows instant visual contact with the penis and discharges therefrom.

SUMMARY OF THE INVENTION

The present invention provides a device for use as a single-use, external male catheter, comprising generally a pliable container having a closed end and an opening so as to receive fluid, an absorbent material, and a liquid-permeable partition separating the closed end from the opening and substantially isolating the absorbent in the interior space of the container between the closed end and the partition. The partition functions to retain the absorbent in an interior portion of the container and to prevent contact between the absorbent and the penis, while also allowing urine to flow to and be contained by the absorbent.

Additionally, the present invention provides a device for use as a single-use external male catheter, comprising generally a pliable container having a closed end and an opening so as to receive fluid, and a closure means including a layer of flexible, vapor permeable material having one side integral with said container and having an adhesive on the other side. The closure means is secured to the patient merely by pressing securely the flexible layer around the penis, and is removed easily by pulling it off the penis (as with an adhesive bandage). A preferred closure means also includes the important aspect of being vapor permeable.

BRIEF DESCRIPTION OF THE DRAWINGS

FIGS. 7 and 9 depict embodiments of the present catheter showing a partition between the closed end and the opening and isolating the absorbent in the closed end.

FIG. 8 depicts a closure means of the present catheter.

DESCRIPTION OF THE PREFERRED EMBODIMENTS

Figure 1:
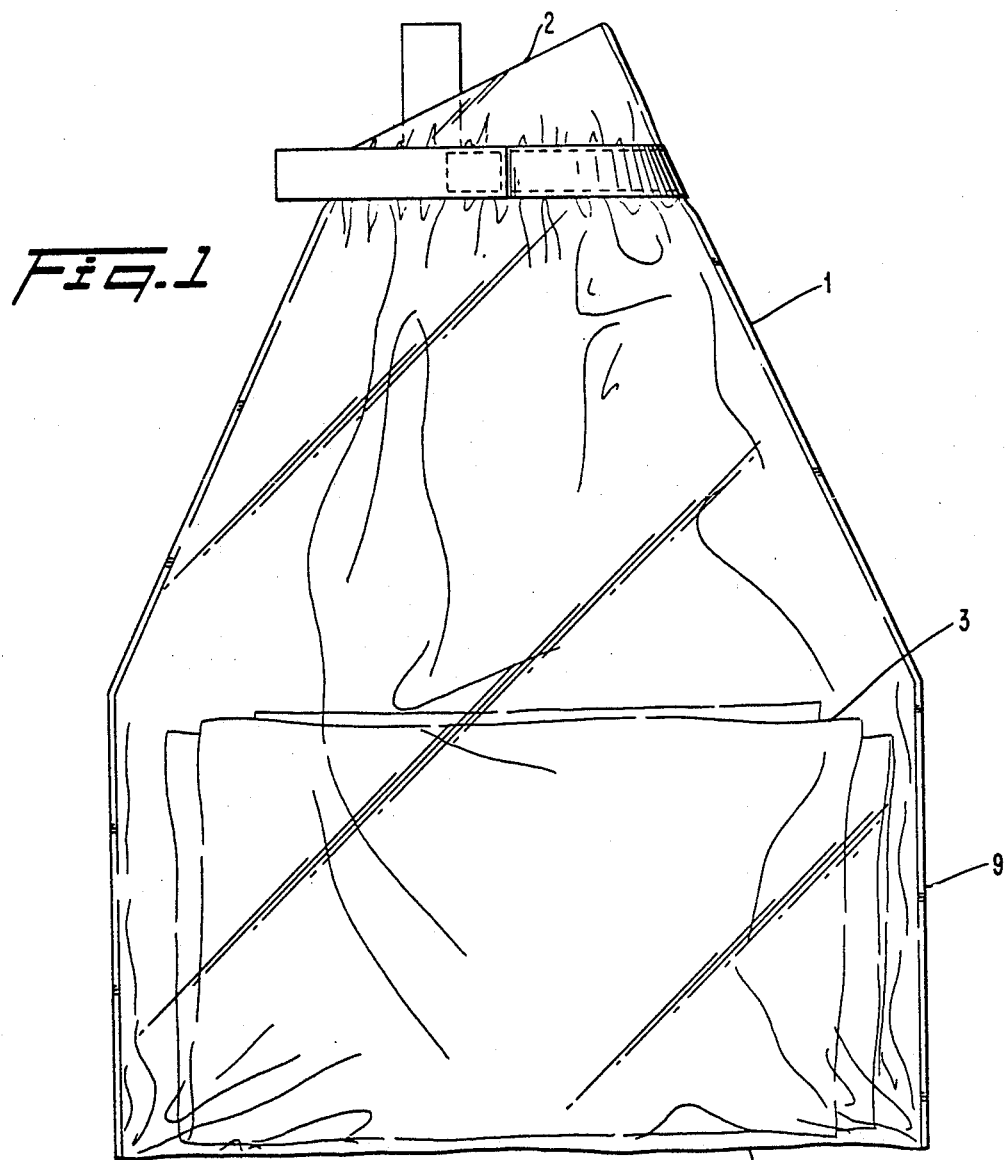
FIG. 1 is a graphic depiction of the catheter of the present invention.
Figure 2:
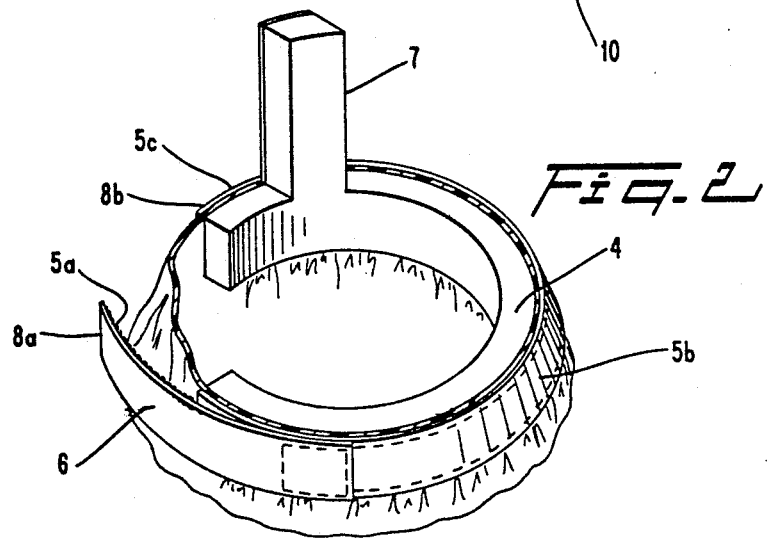
FIGS. 2, 4, 5, and 6 are graphic depictions of closure means for the catheter shown in FIG. 1.

Referring to FIG. 1, there is a pliable, watertight container 1 having therein an absorbent 3 if any conventional material, preferably cotton or cellulose. The container 1 may be made of any suitably thin and pliable material, such as polyethlene or polypropylene. The container is preferably reasonably transparent so that nursing staff may readily view both the penis and the color of the waste fluids to monitor the patient's progress and thereby be alerted to any possible complications. The container has an opening 2 opposite the base into which the penis is inserted and which is preferably formed by the closure device and by the container. The shape of the container may be trapezoidal as shown in FIG. 1, with two short parallel sides 9 adjacent to the base 10, and with the opening being the shortest side; analogously, the container may be purely trapezoidal. In a preferred embodiment, the container is primarily trapezial in shape as shown in FIG. 1, where the opening of the container is angled and not parallel to the base; alternately, and also preferred, the container may be a pure trapezium. In another preferred embodiment the container is hexagonal; similarly, in this embodiment the opening side may be parallel to the base, or substantially non-parallel and angled thereto. It has been found that having the opening side non-parallel to the base results in the container conforming more closely to the shape of the patient's body.

The absorbent may be physically attached to the inside of the container such as by means of an adhesive, or may be an absorbent packet residing inside the container, or may be an absorbent powder.

It will be noted that the container will be of a shape that conforms to the shape of patient's body. The placement of the opening and the shape of the container may therefore be varied to conform to the patient and provide for improved patient comfort. Also preferred is where the catheter is in the shape of a urinal, i.e. somewhat "L" shaped. This L-shaped embodiment is preferred because as the container lies between the patient's legs the absorbent will reside in the bottom of the "L", where discharges would naturally flow due to gravity, and at a point farthest from the penis, thereby avoiding contact between the discharged fluids and the patient's skin.

The closure means is preferably a vapor-permeable and flexible first strip 4 which extends in a second strip 6 beyond the opening of the container having an end 8a and another end 8b and also having a tab 7 attached substantially perpendicular to the first strip. In one embodiment, a portion of the second strip 6 has an adhesive on an inner surface, 5a, and the first strip has an outer surface 5b onto which the adhesive of the second strip will adhere. In a preferred embodiment, the inner surface of the second strip 5a integral with end 8a has a plurality of miniature plastic hooks, and the outer surface 5b of the first strip and/or an outer surface 5c of strip 6 integral with end 8b has a felt-like surface, thereby allowing the first and second strips to be engaged by pressing the surfaces together and disengaged by pulling the surfaces apart. Similarly and also in a preferred embodiment, the surface 5a may have the felt-like material while the surface 4b and/or 5c has the plurality of miniature plastic hooks.

The first strip 4 is of a material which is both soft and permeable to vapor exchange between the interior and the exterior of the container, thereby alleviating irritation due to vapors from the waste products absorbed by the absorbent. In a preferred embodiment, the first strip is of a material such as an air permeable foam rubber which has pores allowing vapor exchange between the interior space and exterior of the bag and which is sufficiently flexible to allow the closure means to expand or contract while maintaining a close fit to the patient. The vapor permeable foams preferably comprise a mesh backing which maintains vapor permeability, provides a support by which foams may be attached to the container, and provides a surface to which the first strip may be selectively attached and removed.

The operation of such preferred embodiment of the catheter of the present invention is as follows. The tab is grasped by the thumb and forefinger of one hand with the middle finger of the same hand extending through the opening into the container. The container is then placed onto the penis and the second strip is wrapped coextensively around the opening until pressure is felt on the middle finger which remains inserted in the bag; the second strip is then secured to the first strip and the middle finger is removed. The middle finger acts essentially to assure that the container is not secured too tightly around the penis. Finally, to assure that the container is not attached too tightly and that there is no vapor lock, the container is squeezed to force air out; the air should flow out reasonably freely and with minimal force applied to the container. It should also be noted that the tab allows the catheter to be handled without contacting portions of the container which may have been in intimate contact with the discharged fluids of the patient.

Another preferred closure means is depicted in FIG. 8. This embodiment includes a layer or strip 82 of vapor-permeable material attached to the portion of the container defining the opening 80. The layer of material extends substantially integrally with the entire opening on the interior portion of the container. Optionally, the layer is attached to the opening and extends therefrom away from container.

An inner side 84 of the layer 82 includes an adhesive layer. The adhesive is of a material which allows opposing inside surfaces of the layer to adhere to each other and to be readily separated by pulling them apart, i.e., selectively engageable. While an adhesive layer is most preferred, any material which is selectively engageable can be used, such as "Velcro" and the like. Adhesive materials are preferred which will also selectively adhere to the penile skin 86, thus further reducing any need for a constrictive closure means.

A preferred structure of the container with the just-described closure means includes a slit 87 in a portion of the container near the opening and extending to the opening. The slit allows for a wider opening to facilitate attachment and removal of the container. Another advantageous structure includes opposing tabs 88. Thus, in operation, easy attachment of the container is achieved by placing the opening of the container over the penile shaft and gently pressing the vapor-permeable layer with the adhesive together and around the penile shaft. Removal of the container is achieved by pulling the layer away from an opposing portion and away from the penis, or alternatively by pulling on the opposing tabs.

Figure 3:
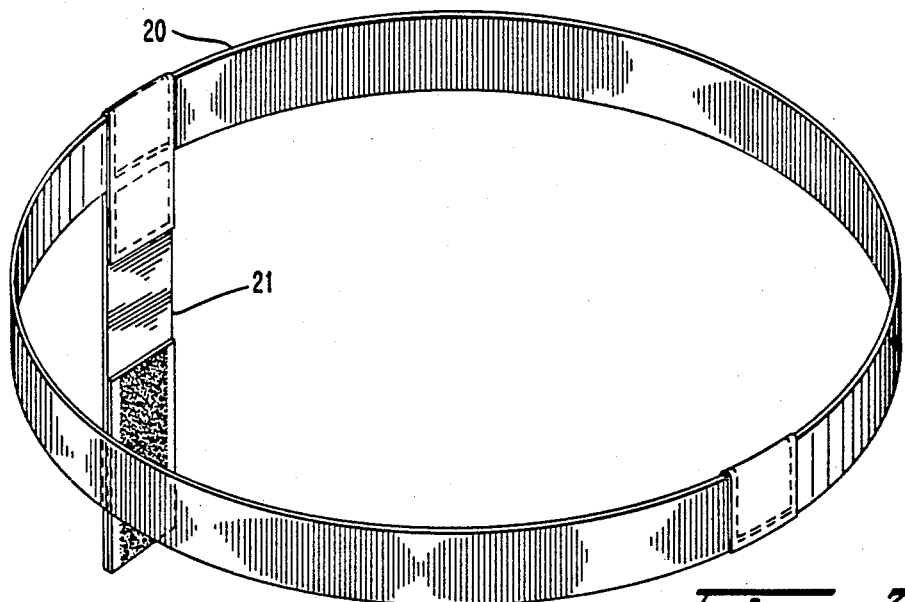
FIG. 3 is a depiction of a waist strap use in connection with the catheter shown in FIG. 1.

An alternative and also preferred embodiment comprises a belt 20, preferably comprising an elastic material, and designed to be worn around the patient's waist and having means to selectively attach to and secure the container, such as a hanging strip 21 as shown in FIG. 3. The hanging strip may be made of a material similar to that of the second strip 6 or of the belt and suitable for attachment thereto. When, for example, the surface 5b has a felt-like material, hanging strip 21 has a plurality of miniature plastic hooks as heretofore described and to which the container may be attached. Alternatively, the belt may have more than one hanging strip. Also alternatively, the container may have one or more strips affixed to the exterior surface of the bag and suitable for attachment to the one or more hanging strips by the means heretofore mentioned or by any such suitable means. Similarly, depending upon the material of which the container is made, the one or more hanging strips may be adhesively attached directly to the container. In essence, any suitable means for selectively attaching the container to the elastic belt which secures the container while the patient moves around and which allows selective removal is sufficient. An important advantage of this embodiment is that the patient is able to freely ambulate and, when necessary, the container is easily removed and a clean container is then attached.

The device as above-described thereby provides for an external single-use male catheter comprising a pliable plastic container provided with a closed end, an opening opposite the closed end so as to receive a fluid, a first strip of flexible vapor-permeable material partially surrounding and integral with a portion of the container defining the opening, and means provided interiorly of the container for absorbing fluid.

The invention thus described performs tasks similar to such devices as condom catheters or incontinence devices, but operates more efficiently and hygienically than those devices. For example, condom catheters not only remain in contact with the patient for extended periods of time, the receptacle containing the waste fluids must be transported to disposal; and if the tube from the catheter to the receptacle is not also replaced; then it too may aggravate hygiene problems by remaining in use for extended periods of time. The present invention overcomes these disadvantages by providing a catheter which is presently disposed of after use; i.e., immediately after use, the entire catheter is disposed of and a new one is fitted to the user. The disposal of the catheter after a single use, and the inexpensiveness thereof, are fundamental to efficiently and inexpensively overcoming the hygiene and operational disadvantages of the catheters currently in use. The objects of the present invention are thus fulfilled by the single-use disposable catheter described herein.

Figure 4:
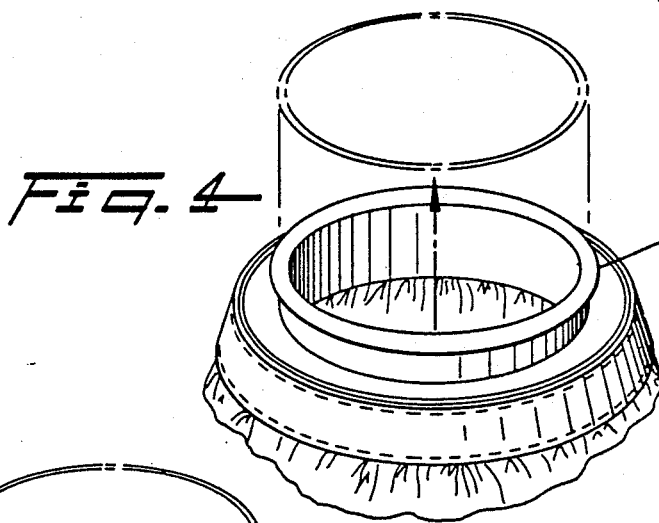
Figure 5:
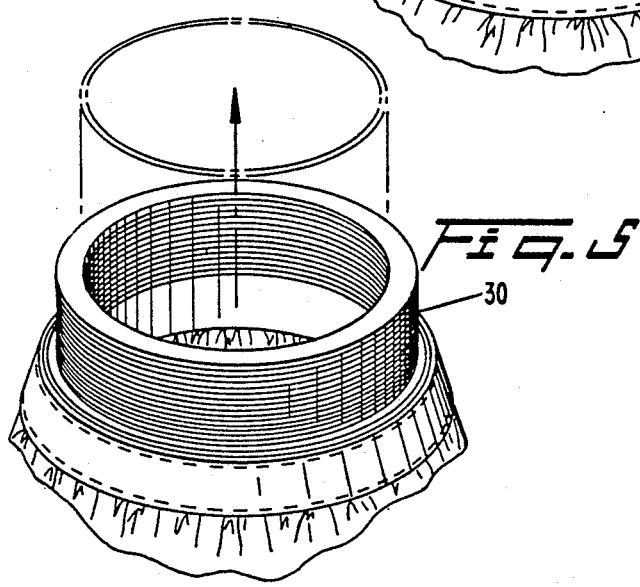

Another closure means contemplated by the present invention utilizes an elastic rubber sleeve. The sleeve may be close-fitting, such as a condom 25, or loose-fitting 30 and secured by an elastic band, as shown in FIG. 4 and FIG. 5, respectively. In these two closure means, the vapor exchange means comprise the vapor-permeable strip such that the patient's skin is integral with the inner surface of the sleeve and the outer surface of the sleeve is integral with the vapor-permeable strip. It will be appreciated that the length of the sleeve is minimal with respect to both the length of the bag and the length of the penis, and is of a length merely sufficient to secure the catheter to the patient for reasonable periods of time, thereby avoiding problems inherent with condom catheters extending substantially the length of the penis. In this embodiment, the penis is inserted into the bag through the sleeve, and is secured by the sleeve itself or by the elastic band around the sleeve.

Figure 6:
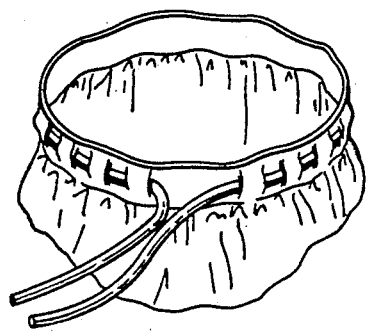

A further closure means contemplated by the present invention is shown in FIG. 6. The portion of the container defining the opening is formed so as to receive a drawstring, such as by hemming and inserting the drawstring or by creating a series of slits through which the drawstring is weaved. To facilitate vapor exchange, the portion of the container formed so as to receive the drawstring and a portion of the container integral therewith have a multiplicity of perforations; so too the drawstring may be perforated. In this embodiment, after the penis is inserted into the bag, the drawstring is loosely tied to secure the bag to the patient.

As noted above, suitable absorbents include absorbent packets, such as cotton, or can include absorbent or superabsorbent powders. For all cases, certain parameters are desirable. It is beneficial to retain the absorbent at a specific location within the container. This prevents the absorbent from being lost or displaced from the container during manufacturing and transport. Fixing the absorbent also decreases the possibility that an absorbent soaked with urine will contact the penis and exacerbate unhygienic conditions.

An absorbent packet or similar structure is fixed by, for example, gluing or heat-sealing same to the closed end of the container, most preferably at that location where urine would flow naturally due to gravity and farthest from the opening.

On the other hand, an absorbent powder is very likely to be displaced from the container or contact the penis. To solve such problems, a device of which a preferred embodiment is shown in FIG. 7 has been developed. The device generally includes a partition 78 between the opening 72 of the container 70 and the closed end 74 of the container, with the absorbent powder 76 retained between the partition and the closed end during manufacture and transportation.

The material of which the partition is formed is liquid-permeable, and can be sturdy or liquid-disintegrable. By "liquid-permeable" is meant materials or structures which allow liquids to pass therethrough, such as gauze or a perforated cloth or plastic sheet. By "liquid-disintegrable" is meant a material which will disintegrate upon exposure to liquid or urine, such as tissue paper. On the other hand, a "sturdy" material is one such as gauze, which does not disintegrate upon exposure to liquid.

The partition thus allows urine to pass into the interior portion of the container in which the absorbent is located, and retains the absorbent during manufacture and shipping. Further, the use of a sturdy partition prevents the urine-soaked absorbent from contacting the penis. A sturdy absorbent, such as gauze, can be made of a material which does not itself absorb urine, or absorbs only to a limited degree, such as various polyester or nylon textiles.

Alternatively, the partition can comprise a pliable plastic sheet having "flap valves." As shown in FIG. 7, each flap valve includes a reasonably large perforation 77 (e.g. 0.25 inch diameter) and a liquid-impermeable flap 75 on the side of the partition adjacent the closed end 74 and the absorbent 76. The flap is attached to the partition 78 at a location 79 adjacent each perforation. In operation, external pressure on the closed end portion of the container tending to force air and absorbent powder out of the container will also tend to seal the flap over the perforation. To prevent bursting, it is preferable to manufacture the container such that the closed end portion of the bag contains as little air as possible. The weight or force of urine contacting the side of the flap adjacent the perforation is sufficient to open the flap and allow urine to pass through to the absorbent. The flap valves will also prevent unabsorbed urine or soaked absorbent from moving back up and contacting the penis.

An alternative valve structure includes a "flutter valve," which is formed by an H-shaped perforation 73 in the partition as shown in FIG. 7. The flutter valve thus essentially has two flaps which are aligned. The size of the perforation, and thus of the valve, and the pliability of the partition material, are chosen such that urine will have the gravitational force to open the valve, but the valve will not easily open and allow displacement of the absorbent powder. In operation, multiple flutter valves are utilized. Alternatively, the flutter valve can be formed with three perforations in the shape of a tricuspid valve.

Optionally, the partition is a solid, non-permeable sheet which is designed to retain the absorbent until the catheter is used, at which time the entire sheet is removed.

An alternative embodiment includes a container-within-a-container, as depicted in FIG. 9. The penis is inserted into an inner container or sleeve 90 which is attached at one end to the opening portion 92 of the container. At the other end of the sleeve 94 is the partition as previously described with reference to FIG. 7. The sleeve can be made substantially longer than the penis, thereby essentially acting to isolate the penis from the absorbent. Further, the portion of the sleeve extending farther than the penis will collapse due to the pliability of the material, which further isolates the penis from the absorbent material. In such an embodiment, the partition most preferably comprises tissue paper.

The invention thus described achieves its objective by providing a disposable single-use catheter and by providing a catheter having a flexible vapor-permeable material integral with the opening. The objectives of the present invention are also achieved by the embodiments described in the specification.

Thus, the principles, preferred embodiments and mode of operation of the present invention have been described in the foregoing specification. The particular embodiments disclosed are not intended to limit what is to be protected and hence are to be regarded as exemplary rather than restrictive; variations and changes may be made by others without thereby departing from the spirit of the present invention. Accordingly it is expressly intended that all variations and changes which fall within the spirit and scope of the present invention as defined by the claims be embraced thereby.

What is claimed is:

1. A device for use as an external-single use catheter, comprising: a pliable plastic container having an interior space and provided with a closed end; an opening in said container opposite said closed end; a liquid-permeable partition located in said interior space integral with said container substantially separating said opening from said closed end, wherein said partition comprises a liquid-disintegrable material; and an absorbent means provided in said interior space defined by said closed end and said partition.

2. The device as defined by claim 1, wherein said partition comprises tissue paper.

3. The device as defined by claim 1, wherein said partition comprises a pliable, non-permeable sleeve, one end of said sleeve being attached to a portion of said container defining said opening and another end of said sleeve being sealed by a liquid-permeable material, and wherein said liquid-permeable material is a disintegrable material.

* * * * *